United States Patent [19]

Parker

[11] Patent Number: 4,907,132

[45] Date of Patent: Mar. 6, 1990

[54] LIGHT EMITTING PANEL ASSEMBLIES AND METHOD OF MAKING SAME

[75] Inventor: Jeffrey R. Parker, Concord, Ohio

[73] Assignee: Lumitex, Inc., North Royalton, Ohio

[21] Appl. No.: 242,898

[22] Filed: Sep. 12, 1988

Related U.S. Application Data

[63] Continuation-in-part of Ser. No. 171,844, Mar. 22, 1988.

[51] Int. Cl.[4] .............................................. F21Y 8/00
[52] U.S. Cl. ........................................ 362/32; 362/31; 350/96.3
[58] Field of Search ................. 362/32, 31, 253, 293, 362/418; 128/303.1, 395, 397, 398; 350/96.20, 96.22, 96.3

[56] References Cited

U.S. PATENT DOCUMENTS

| | | | |
|---|---|---|---|
| 1,725,357 | 8/1929 | Kleeman | 128/395 |
| 3,508,589 | 4/1970 | Derick et al. | 139/420 R |
| 3,596,083 | 7/1971 | Lovering | 362/32 |
| 3,718,814 | 2/1973 | Van Slyke | 362/32 |
| 3,825,336 | 7/1974 | Reynolds | 362/32 |
| 4,128,759 | 12/1978 | Hunt et al. | 362/32 |
| 4,233,493 | 11/1980 | Nath | 128/398 |
| 4,234,907 | 11/1980 | Daniel | 362/32 |
| 4,241,382 | 12/1980 | Daniel | 362/255 |
| 4,385,344 | 5/1983 | Gonser | 362/32 |
| 4,422,719 | 12/1983 | Orcutt | 350/96.3 |
| 4,466,697 | 8/1984 | Daniel | 350/96.3 |
| 4,519,017 | 5/1985 | Daniel | 362/32 |
| 4,597,030 | 6/1986 | Brody et al. | 362/32 |
| 4,650,280 | 3/1987 | Sedlmayr | 362/32 |
| 4,761,047 | 8/1988 | Mozi | 362/32 |

*Primary Examiner*—Ira S. Lazarus
*Assistant Examiner*—Richard R. Cole
*Attorney, Agent, or Firm*—Renner, Otto, Boisselle & Sklar

[57] ABSTRACT

Light emitting panel assemblies and method of making same include one or more layers of woven fiber optic material having disruptions or bends at discrete locations along the length of the fibers to allow light to be emitted therefrom. Only selected areas of the disruptions or bends are coated with a suitable coating material that has a refractive index that changes the attenuation of the light emitted from the selected areas. The coating material may be applied to the selected areas using one or more carrier members which become part of the panel. Alternatively, a non-permanent carrier such as a roller may be used to coat selected areas of the optical fiber disruptions or bends with the coating material after the weaving process.

62 Claims, 3 Drawing Sheets

LIGHT EMITTING PANEL ASSEMBLIES AND METHOD OF MAKING SAME

CROSS REFERENCE TO RELATED APPLICATIONS

This application is a continuation-in-part of applicant's copending U.S. patent application Ser. No. 171,844, entitled "Fiber Optic Light Emitting Panel and Method of Making Same", filed Mar. 22, 1988, which is incorporated herein by reference.

BACKGROUND OF THE INVENTION

This application relates to certain improvements in light emitting panel assemblies including one or more panels made of woven optical fibers having a fiber optic light pipe connected to one or both ends for transmitting light to the panel from a remote light source. Light is caused to be emitted from the panel by disrupting the surface of the optical fibers in the panel area as by scratching or otherwise deforming as by bending the optical fibers at a plurality of discrete locations along their length such that the angle of bend approximately exceeds the angle of internal reflection. The percentage of light emitted from each bend is proportional to the bend radius and arc length. By controlling the weave spacing and pattern of the woven optical fibers, one can control the shape and radius of the bends at any location on a woven panel to thereby control the desired light output pattern from the panel.

A fiber optic light emitting panel generally of this type is disclosed in applicant's aforementioned copending U.S. application Ser. No. 171,844. Also, as further disclosed in such copending application, the optical fibers can be coated with a material having a refractive index that will cause a change in the attenuation of the optical fibers in the light emitting portion of the panel to increase the optical efficiency of the panel. The amount of attenuation can be varied by varying the index of refraction and thickness of the applied coating.

In applications where the coating is applied to the entire length of the fibers in the light emitting portion of the panel, or such light emitting portion is completely encapsulated in such a coating, attenuation changes will occur over the entire light emitting portion. In other applications where increased optical efficiency is desired, it would be desirable to cause attenuation changes only at selected areas of the panel from which light is normally emitted.

SUMMARY OF THE INVENTION

With the foregoing in mind, it is a principal object of this invention to further increase the optical efficiency of a fiber optic light emitting panel by attenuating the light output only at selected areas of the panel from which light is normally emitted.

Another object is to provide relatively uniform light output over such selected areas of the panel.

A further object is to provide such a light emitting panel that emits optical energy at predetermined exit ray angles to fit a particular application.

Still another object is to provide a method of fabricating such a light emitting panel that is easily automated for production.

These and other objects of the present invention may be achieved by applying an attenuation producing coating to selected areas of the optical fibers of the panel from which light is normally emitted to cause attenuation changes in such selected areas to increase the overall optical efficiency of the panel.

In a preferred panel assembly disclosed herein, the optical fibers in the panels include disruptions or bends that emit a percentage of light along their length, and the attenuation producing coating is applied only to the outer surface of selected disruptions or bends to cause attenuation changes in the light that is normally emitted from such disruptions or bends. Coatings having different refractive indexes may be used to coat different light emitting areas to cause a higher attenuation of light from those areas where light is usefully emitted and a lower attenuation of light from other areas where it is not.

Also in accordance with the invention, the attenuation producing coatings may be applied to selected light emitting areas of the woven optical fiber panel using a carrier member that may but need not become a permanent part of the panel. The carrier itself may be the coating or may be a highly reflective film that is only coated on the side facing the panel to redirect the light that is emitted from that side back through the panel and out the opposite side thereof.

In still another form of the invention, the carrier may be a metal back reflector, or metal inserts may be inserted into the panel to permit the panel to be formed into a particular shape.

Further in accordance with the invention, the amount of attenuation at a particular light emitting area on the optical fibers may be controlled by controlling the amount of the light emitting area that is covered by the coating.

If desired, the light emitting portion of the panel may be caused to emit light substantially from one side only by applying a higher index of refraction coating to the light emitting areas on such one side and a lower index of refraction coating to the light emitting areas on the other side, thus minimizing the percentage of light that is being emitted from the other side which may be reflected back through the panel using a back reflector.

Further in accordance with the invention, the panel may contain multiple woven optical fiber layers, with carriers coated on both sides with the same or different index of refraction coatings interposed between such layers.

Still further in accordance with the invention, the carrier may be a prismatic or lenticular lens to redirect the exit light ray angles for a particular application. Also, the carrier may be a filter to absorb or reflect certain frequencies of radiation.

Further in accordance with the invention, the carrier may act as a support to hold the weave spacing and pattern of the woven optical fibers in position. Also, the carrier may be used to protect the panel from hazardous environments and permit easy cleaning and/or sterilization of the panel. Furthermore, the carrier may be a resin or epoxy coating film that is heat or radiation cured upon assembly.

In accordance with another aspect of the invention, the carrier may be a diffuser or transreflector to defuse light emanating from the panel and reflect ambient light.

Alternatively, a roller or other non-permanent carrier may be used to apply an attenuation producing coating to selected light emitting areas of the panel. By controlling the roll pressure and using different types of rollers, one can control the size, shape and location of the coated area on the optical fibers.

Further in accordance with the invention, impurities may be added to the coating to cause increased attenuation or diffusion of light. Also, the added impurities may absorb or reflect predetermined frequencies of radiation.

Still further in accordance with the invention, the optical fibers at one or both ends of the panel are bundled together to form an optical cable for transmitting light to the panel from a remote light source. At the outermost end of the cable is a connector assembly including baffle means surrounding the fiber ends. Also, a window or filter may be adhesively bonded to the polished end of the connector assembly.

To the accomplishment of the foregoing and related ends, the invention, then, comprises the features hereinafter fully described and particularly pointed out in the claims, the following description and the annexed drawings setting forth in detail certain illustrative embodiments of the invention, these being indicative, however, of but several of the various ways in which the principles of the invention may be employed.

DETAILED DESCRIPTION OF THE PREFERRED EMBODIMENTS

Figure 1:
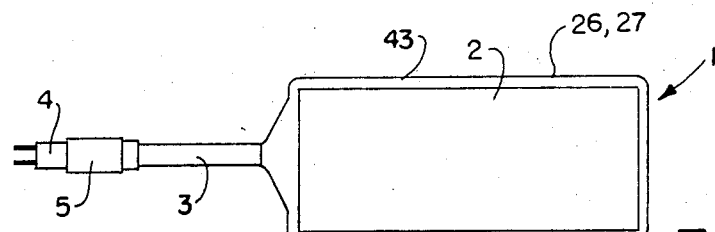
FIG. 1 is a schematic top plan view of one form of light emitting panel assembly in accordance with this invention including a single panel.
Figure 2:
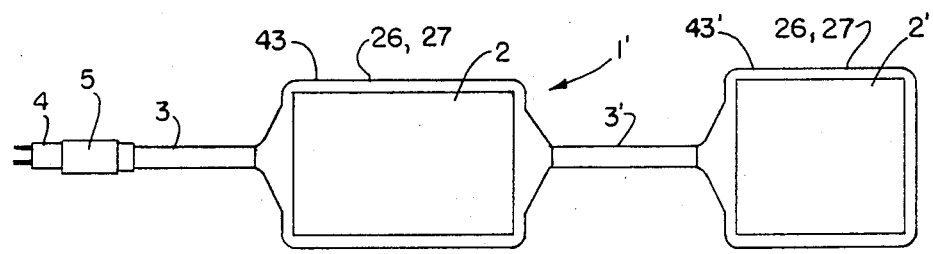
FIG. 2 is a schematic top plan view of another form of light emitting panel assembly in accordance with this invention including plural panels.

Referring now in detail to the drawings, and initially to FIGS. 1 and 2, there are schematically shown two different panel assemblies 1 and 1' in accordance with this invention each including one or more light emitting panels 2, 2' having light cables 3 at one or both ends to transmit light from a remote light source 4 to the light emitting panel. At the outermost end of the optical cable 3 is a connector assembly 5 which serves as an interface between the light source 4 and the optical fiber ends. The panel assembly 1 shown in FIG. 1 includes a single light emitting panel 2, with an optical cable 3 and connector assembly 5 at one end thereof, whereas the panel assembly 1' shown in FIG. 2 includes two light emitting panels 2, 2' interconnected together by means of an optical cable 3' and having another optical cable 3 connected to the panel 2 with a connector assembly 5 and light source 4 at the outermost end thereof.

Each light emitting panel 2 (or 2') may be made of one or more layers 10 of optical fibers 11 which may be woven into a sheet or mat in the manner disclosed, for example, in U.S. Pat. No. 4,234,907 granted to Maurice Daniel on Nov. 18, 1980, the disclosure of which is incorporated herein by reference. In the example shown in FIG. 3 of the present application, the light emitting panel 2 consists of one woven optical fiber layer 10, whereas in the example shown in FIG. 5, the panel consists of two such layers 10, 10'. Preferably, the optical fibers 11 of each layer are woven only in the warp direction, with fill threads 12 woven in the weft direction. However, it should be understood that the fill threads 12 could also be optical fibers if desired. The weft threads are the threads usually carried by the shuttle of a weaving loom, whereas the warp threads extend lengthwise of the loom, crossed by the weft threads.

Each optical fiber 11 may be made from one or more optical fiber strands each including a light transmitting core portion of a suitable transparent material and an outer sheath or cladding of a second transparent material having a relatively lower index of refraction than the core material to assist in preventing the escape of light along its length. The core material can be made of either glass or plastic or a multi-strand filament having the desired optical characteristics. The index of refraction of the outer sheath material is less than that of the core material, whereby substantially total reflection is obtained at the sheath-core interface, as well known in the art.

Figure 3:
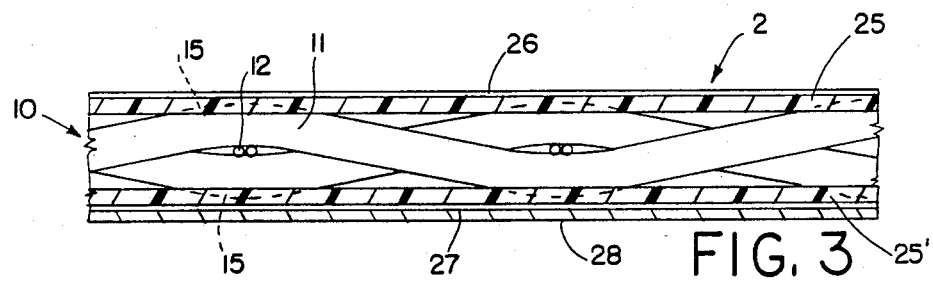
FIG. 3 is an enlarged schematic fragmentary longitudinal section through any one of the light emitting panels of FIGS. 1 and 2.
Figure 5:
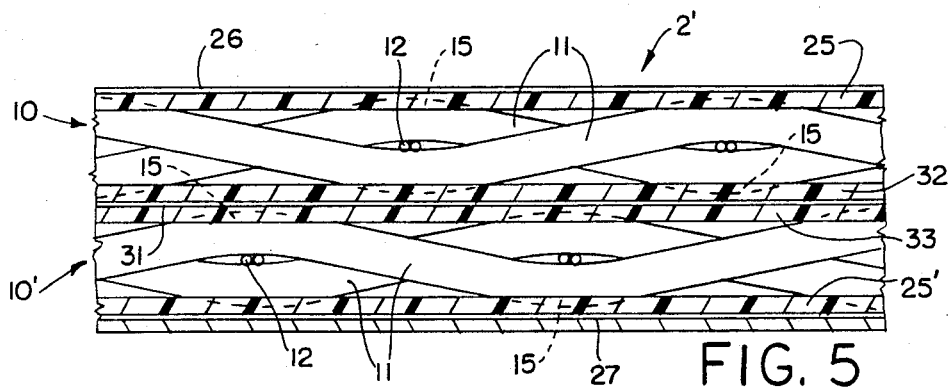
FIG. 5 is an enlarged schematic fragmentary longitudinal section through another form of light emitting panel in accordance with this invention.

To cause light to be emitted from each light emitting panel 2, the external surface of the optical fibers 11 may be disrupted as by bending the optical fibers 11 at a plurality of discrete locations along their lengths as schematically shown in FIGS. 3 and 5 such that the angle of each bend 15 approximately exceeds the angle of internal reflection so that a portion of the light will be emitted at each bend 15.

Figure 4:
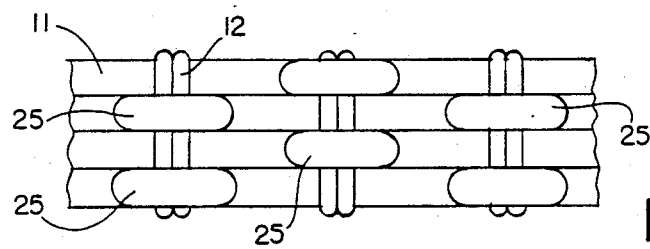
FIG. 4 is a schematic fragmentary top plan view showing attenuation producing coatings applied to selected light emitting areas of the panel of FIG. 3.

The uniformity of illumination of each light emitting panel 2 may be varied by varying the shape of the optical fiber disruptions or bends 15 and/or the spacing between such disruptions or bends as by varying the pattern and tightness of the weave or by varying the proportion of opticl fibers 11 to other material in the weave. The illumination can, for example, be increased by placing the disrutions or bends 15 closer together or by making the weave progressively tighter as the distance from the light source 4 increases. Using fill threads 12 having different coefficients of friction will also help to control the tightness of the weave, in that the higher the coefficient of friction, the tighter it is possible to weave the optical fibers 11. Also, a plurality of fill threads 12 may be used as further schematically shown in FIGS. 3-5 to provide more surface points for increased friction, and to reduce the thickness of each individual fill thread and thus the thickness of the panel 2 while still achieving substantially the same rigidity provided by a thicker fill thread.

Figure 7:
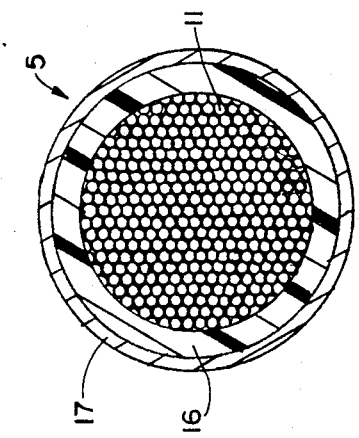
FIG. 7 is a transverse section through the connector assembly of FIG. 6 taken generally on the plane of the line 7—7 thereof.
Figure 6:
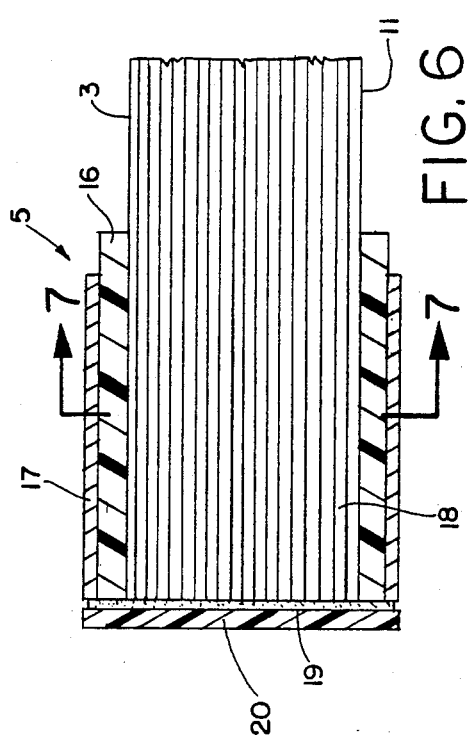
FIG. 6 is an enlarged schematic longitudinal section through the connector assembly of FIGS. 1 and 2.

The optical fibers 11 at one or both ends of each panel 2 may be brought together and bundled to form either a ribbon cable or a round cable 3 as desired to transmit light from the remote light source 4 to one or more light emitting panels 2. At the outermost end of the optical cable 3 is the connector assembly 5 which, as shown in greater detail in FIGS. 6 and 7, may consist of a buffer material 16 surrounding the gathered optical fibers 11 and a ferrule 17 crimped onto the buffer material which squeezes the buffer material and packs the optical fiber ends 18 solid.

The buffer material 16 may be made of any suitable material such as Teflon that will protect the optical fibers 11 from the ferrule 17 during the crimping operation. Alternatively, the ferrule 17 itself may be made out of a suitable buffer material, thus eliminating the need for a separate baffle. The buffer material desirably has a low refractive index so that it does not cause high attenuation on the surface of the optical fibers 11 contacted thereby.

If desired, the connector assembly 5 may be heated during the crimping operation to soften the buffer material 16 or optical fibers 11 to permit them to be deformed to the desired cross-sectional shape, for example, to that of a polygon. After crimping, the cable end 19 may be cut off and polished to the desired finish.

Both the ferrule 17 and buffer material 16 may have a lip or flange thereon to provide a locating point or surface thereon. Also, if the optical fibers 11 are made of plastic, the connector assembly 5 may be heat treated to preshrink the optical fibers 11 before polishing to produce a higher operating temperature limit.

After polishing, the polished end 19 of the connector assembly 5 may be coated with a suitable coating that reflects certain wavelengths of light. Also, a window or filter 20 may be adhesively bonded to the polished end 19 of the connector assembly 5.

The light source 4 may be of any suitable type including any of the types disclosed in applicant's copending U.S. application Ser. No. 125,323, filed Nov. 24, 1987, which is also incorporated herein by reference. If desired, such light source 4 may be epoxied directly to the polished end 19 of the connector assembly 5 or to the window or filter 20 interposed therebetween.

A cross-sectional view of one form of light emitting panel 2 in accordance with this invention is schematically shown in FIG. 2 wherein a transparent coating 25 having a different refractive index than the core material of the optical fibers 11 is applied to selected light emitting areas of the panel to cause changes in the attenuation of light being emitted from the panel. Preferably, the coating 25 is only applied to the outer surfaces of the disruptions or bends 15 on one or both sides of each optical fiber layer 10. This increases the overall optical efficiency of the panel 2 by causing attenuation changes only where the light normally escapes from the disruptions or bends 15 of the woven optical fiber panel 2.

In the example shown in FIG. 2, suitable coatings 25, 25' are applied to the outer surfaces of the optical fiber disruptions or bends 15 on both sides of the panel 2. One method of applying such coatings to selected bend areas of the woven optical fibers 11 is to use the same or different carrier members 26, 27 to laminate the coatings to opposite sides of the optical fiber panel. The material of the carrier members 26, 27 may vary depending on the particular application. For example, carrier member 26 may be made of a clear plastic film having a suitable coating 25 on one side only for coating one side of the panel 2, whereas the other carrier member 27 may have a coating 25' on one side for coating the other side of the panel and a highly reflective film 28 on the other side. Such a reflective film carrier member 27 also acts as a back reflector to redirect the light that is emitted from the other side back through the panel and out through the one side. Also, the carrier member may be the coating itself. For example, a Teflon film may be used both as the carrier and coating.

The amount of attenuation at a particular disruption or bend 15 may be controlled by changing the amount of surface area of the bend 15 which is covered by the coating 25, 25'. This may be determined, for example, by the type of press rolls and amount of pressure used to apply the carrier members 26, 27 to the optical fiber layer 10 during the laminating process. For example, a higher pressure applied to the carrier members 26, 27 by press rolls 29, 30 (see FIG. 8) having a softer rubber sleeve will produce a greater coated area. Also, by varying the pressure of the press rolls 29, 30 as the laminating proceeds along the length of each panel, one can gradually increase or decrease the coated area on the optical fiber bends 15 to adjust the uniformity of light output from such bends.

The areas of the optical fibers 11 not in direct contact with the coatings 25, 25' are encapsulated by air. By changing the index of refraction of the coatings 25, 25' relative to the index of refraction of air, one can change the ratio of attenuation between a coated and non-coated area of the optical fiber panel 2. Such coatings 25, 25' may be a solid, liquid or gas.

If it is desired to emit light substantially only from one side of the panel 2, a higher index of refraction coating 25 may be applied to the outer surface of the bends 15 on one side of the panel 2, and a lower index of refraction coating 25' applied to the outer surface of the bends 15 on the other side of the panel. The lower index coating substantially reduces the amount of light emitted from the other side of the panel, which in turn substantially reduces the percentage of light that has to be reflected back through the panel. The net result is that the overall optical efficiency of the panel is increased because absorption and scattering losses due to back reflection of light are lowered.

When the optical fiber panel 2' contains multiple optical fiber layers 10, 10' as shown in FIG. 5, a carrier member 31 having the same or different index of refraction coatings 32, 33 on opposite sides thereof may also be laminated between the optical fiber layers 10, 10' so that the respective coatings 32, 33 will contact the outer surfaces of the bends 15 on the inwardly facing sides of the optical fiber layers.

Figure 9:
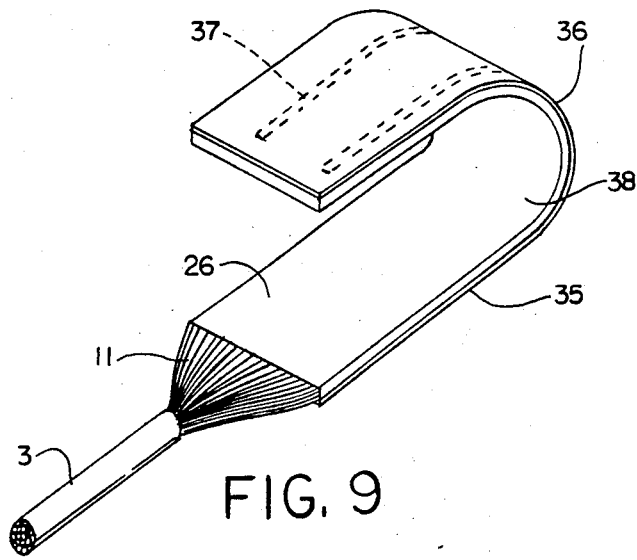
FIGS. 9, 11 and 12 are schematic illustrations showing different shapes of panels constructed in accordance with the present invention.

If desired, carriers 26, 27, 31 may be a resin or epoxy-coated film which may be heat or radiation cured upon assembly. Also, one of the carriers 35 may be a metal back reflector 36, or metal inserts 37 may be inserted into the panel 38 so that the panel can be bent or formed to a particular shape as schematically shown in FIG. 9.

These various carriers 26, 27, 31 may also be used as a support to hold the weave spacing and pattern in position. Furthermore, such carriers may be used as a top coat for the woven optical fiber panel 2 to provide protection for the panel from hazardous environments. This would make the panel assembly 1 particularly suitable for use in certain medical or dental applications where it is necessary to clean or sterilize the assembly after each use.

Carrier 26 (shown in FIGS. 3 and 5) may also be a prismatic or lenticular film to redirect exit light ray angles for a particular application. Alternatively, carrier 26 may be a glass or plastic filter that absorbs or reflects certain frequencies of light. Likewise, carrier 26 may be a diffuser or transreflector which diffuses light emitted from the woven optical fiber panel 2 and reflects ambient light. This type of assembly 1 could be used to back light a liquid crystal display, where ambient light is used for viewing when available and the optical fiber panel 2 is used as a back light during low ambient levels.

Figure 8:
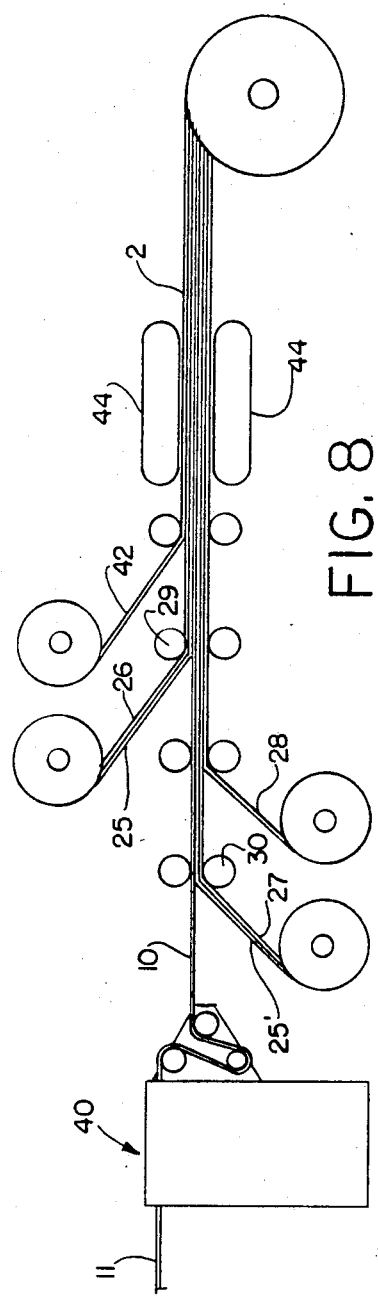
FIG. 8 is a schematic illustration of one form of laminating system for use in making any of the panels of FIGS. 1-5.

FIG. 8 schematically shows a laminating system for making light emitting panels of the type disclosed herein using a loom 40 for weaving one or more layers 10 of optical fiber material 11. As the optical fiber layer 10 comes off the loom 40, one or both surfaces of the optical fiber layer 10 may be coated with a coating 25, 25' having the same or different refractive indexes using suitable carriers 26, 27. Also, a suitable back reflector 28 may be applied to the exterior of carrier 27, and a clear film or diffuser 42 may be applied to the exterior of carrier 26. Suitable heaters 44 may be used to apply heat to opposite sides of the panel material, and the carriers 26, 27 may be sealed around the periphery 43, 43' of each panel 2, 2' to provide a protective barrier for each panel 2, 2' as schematically shown in FIGS. 1 and 2.

Figure 10:
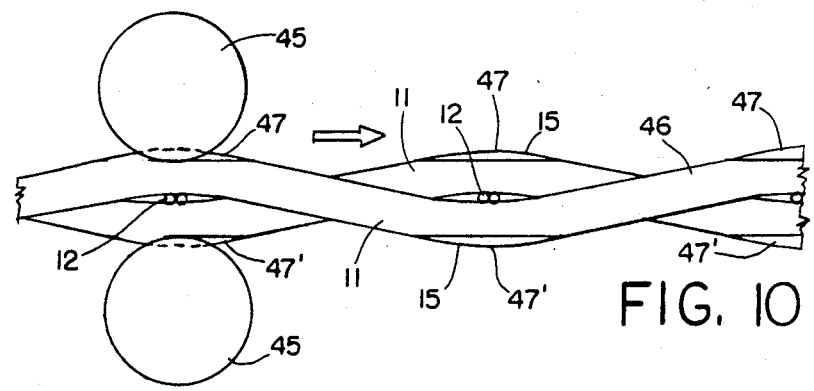
FIG. 10 is a schematic illustration of another form of laminating system for use in making a modified form of panel.

In lieu of using permanent carriers 26, 27 for applying the coating material 25, 25', a non-permanent carrier such as a roller 45, 45' may be used to coat the outer surface of the bends 15 of a woven optical fiber panel 46 with a suitable coating 47, 47' after the weaving process, as schematically shown in FIG. 10. A non-permanent carrier is anything that applies a coating 47, 47' to selected areas of the optical fiber panel 46 and does not become part of the final assembly. The roll pressure and roller surface type can be controlled to control the size, shape and location of the coated areas 47, 47' on the optical fiber bends 15. Also, if desired, a coating with a high vapor pressure or a heat or radiation durable coating may be used as the coating material to decrease panel assembly time due to the fast cure rate of the coating material.

Regardless of which method is used to apply the coating to selected normal light emitting areas of the optical fiber panels, impurities may be added to the coating to cause increased attenuation or diffusion of light. Also, the added impurities may be used to absorb or reflect predetermined frequencies of radiation. Moreover, the coating may if desired be used to completely or partially dissolve the outer sheath or cladding that surrounds the light transmitting core portion of each optical fiber.

Such light emitting panel assemblies may be used for different applications, including back lighting, photo therapy treatment, and light curing of adhesives and the like. Typcial back lighting applications would be back lighting liquid crystal displays or transparencies and the like. Such woven optical fiber panels in accordance with this invention can be laminated directly to or inserted behind a liquid crystal display. For smaller liquid crystal displays, a light emitting diode may be epoxied to a cable end of the panel assembly to provide adequate back light and as much as 100,000 hours life. For larger panels, incandescent bulbs, arc lamps, the sun, or other light sources may be used.

Figure 11:
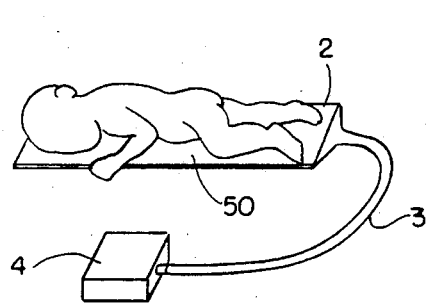
Figure 12:
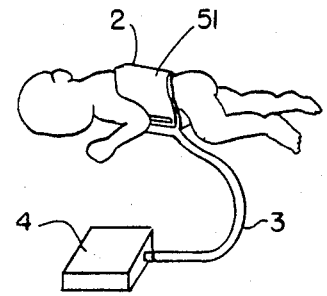

To facilitate use of such light emitting panel assemblies for photo therapy, the panels may be formed in the shape of a pad, belt, collar, blanket, strap, or other such shape. FIG. 11 schematically shows a panel 2 in the shape of a pad 50, whereas FIG. 12 schematically shows a panel 2 in the shape of a belt 51. In either case, the panel 2 may be placed in direct contact or near a patient such as a newborn baby to provide photo therapy treatment for jaundice or the like. Presently, such treatment is administered using banks of fluorescent lights or single incandescent reflector lamps. Jaundice is dissipated by light in approximately the 450-500 nanometer range. Placing the light emitting panel 2 in direct contact with the patient as shown in FIGS. 11 and 12 causes a greater percentage of light, at a higher intensity, to be transmitted to the patient. Undesired wavelengths of light may be filtered out at the light source to produce a cold light emitting panel free of harmful infrared or ultraviolet radiation. Also, electrical energy is removed from the treatment area because of the fiber optic light cable 3 which permits use of a remote light source 4 such as an incandescent lamp, arc lamp, or the like. If a tungsten halogen lamp is used, the halogens may be adjusted such that the lamp emits a greater percentage of radiation in the treatment frequency range.

Another example of how the light emitting panels of the present invention may be used is in the radiation curing or light curing of adhesives or epoxies and the like. Light cured adhesives are used in a variety of applications, including aerospace, dental, photography, circuit board, and electronic component manufacture. With the proper light source, the woven fiber optic panels of the present invention will produce high intensity uniform light to any desired area. Higher intensity light produces faster curing times to greater depths. Also, uniform light output produces even curing over an entire surface or object and reduces internal stress. The light emitting panels may be fabricated such that they are flexible and can conform to the surface or part being cured, and can be fabricated such that they are an internal part of an assembly that is self curing or can be used in curing. The remote light source also allows the use of the light emitting panels of the present invention in dangerous or inaccessible locations, or where electricity, heat, EMI or RFI are problems.

Although the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the claims.

What is claimed is:

1. A light emitting panel having one side and an other side opposite said one side comprising a plurality of optical fibers having bends at discrete locations along the length of said fibers to allow light to be emitted therefrom, and coating means applied only to selected areas of the outer surfaces of said bends, said coating means extending part way around the sides of said bends and having a refractive index that changes the attenuation of the light emitted from said selected areas.

2. The panel of claim 1 wherein coating means having a higher index of refraction than said optical fibers is applied to said selected areas on said one side of said panel.

3. The panel of claim 2 wherein coating means having a lower index of refraction than said optical fibers is applied to said selected areas on the other side of said panel.

4. The panel of claim 1 wherein coating means having the same refractive index is applied to said selected areas on both sides of said panel.

5. The panel of claim 1 wherein said coating means on one side of said panel has a different index of refraction than said coating means on the other side of said panel.

6. The panel of claim 1 further comprising carrier means for said coating means.

7. The panel of claim 6 wherein said carrier means for said coating means on the other side of said panel includes a back reflector to redirect the light that is emitted from said other side back through said panel and out through said one side.

8. The panel of claim 6 wherein said carrier means has said coating means on one side only of said carrier means.

9. The panel of claim 6 wherein said carrier means comprises a resin or epoxy-coated film that is heat or radiation cured upon assembly.

10. The panel of claim 6 wherein said carrier means includes a prismatic or lenticular film to redirect exit light ray angles of light emitted from said panel.

11. The panel of claim 6 wherein said carrier means includes a filter for absorbing or reflecting certain frequencies of light emitted from said panel.

12. The panel of claim 6 wherein said carrier means includes a diffuser or transreflector which diffuses light emitted from said panel and reflects ambient light.

13. The panel of claim 6 wherein said carrier means is made of said coating means.

14. The panel of claim 1 further comprising carrier means for said coating means, said carrier means also acting as a support to hold the weave spacing and pattern of said woven optical fibers in position.

15. The panel of claim 1 further comprising carrier means for said coating means, said carrier means forming a top coat for said panel to provide protection for said panel.

16. The panel of claim 1 further comprising a back reflector on the other side of said panel.

17. The panel of claim 16 wherein said back reflector is made of metal which is bendable to permit said panel to be formed into a desired shape.

18. The panel of claim 1 further comprising insert means for permitting said panel to be formed into a desired shape.

19. The panel of claim 1 further comprising separate carrier means for applying said coating means to selected areas of said disruptions or bends on opposite sides of said panel, said carrier means being heat sealed around the periphery of said panel to provide a protective barrier for said panel.

20. The panel of claim 1 which includes plural layers of said optical fibers, and coating means only on selected areas of the outer surfaces of said bends on both sides of each of said layers of said optical fibers.

21. The panel of claim 20 further comprising carrier means interposed between adjacent layers having coating means on opposite sides thereof for applying said coating means to selected areas of the outer surfaces of said bends on opposing sides of said adjacent layers.

22. The panel of claim 21 wherein said coating means on opposite sides of said carrier means have the same index of refraction.

23. The panel of claim 21 wherein said coating means on opposite sides of said carrier means have different indexes of refraction.

24. The panel of claim 21 which includes a plurality of layers of said optical fibers, said coating means being applied to selected areas of the outer surfaces of said bends on both sides of each of said layers of said optical fibers.

25. The panel of claim 1 wherein said coating means is only applied to the outer surfaces of said bends on one side of said panel to change the attenuation of light emitted from said one side.

26. The panel of claim 1 wherein said coating means is only applied to the outer surfaces of said bends on both sides of said panel to change the attenuation of light emitted from said panel.

27. The panel of claim 1 wherein the outer surfaces of said bends are partially embedded in said coating means.

28. The panel of claim 1 wherein the area of the outer surfaces of said bends that is covered by said coating means varies along the length of said panel to adjust the uniformity of light output from said panel.

29. A panel assembly comprising a light emitting panel made of a plurality of optical fibers having bends at discrete locations along the length of said fibers to allow light to be emitted therefrom, coating means applied only to selected areas of the outer surfaces of said bends, said coating means extending part way around the sides of said bends and having a refractive index that changes the attenuation of the light emitted from said selected areas, a light cable connected to said panel for transmitting light to said panel from a remote light source, and connector means at a remote end of said cable which serves as an interface between said light cable and remote light source.

30. The panel assembly of claim 29 further comprising a second light emitting panel connected to said first mentioned panel by another light cable extending between said panels for transmitting light from said first mentioned panel to said second panel.

31. The panel assembly of claim 29 wherein said light cable is formed by bundling the optical fibers together at one end of said panel, and said connector means comprises buffer means surrounding the remote end of said light cable.

32. The panel assembly of claim 31 further comprising ferrule means crimped onto said buffer means said buffer means being made of a material that will protect the optical fibers of said light cable from said ferrule means during crimping.

33. The panel assembly of claim 31 wherein said buffer means is made of a material having a low refractive index.

34. The panel assembly of claim 31 further comprising ferrule means crimped onto said buffer means to squeeze said buffer means and pack the optical fiber ends of said cable substantially solid.

35. The panel assembly of claim 34 wherein said remote end of said light cable is heat treated to preshrink said optical fibers at said remote end before crimping to produce a higher operating temperature limit.

36. The panel of claim 34 wherein said optical fibers are made of plastic.

37. The panel of claim 34 wherein the optical fiber ends are deformed during crimping such that the shape of the cross-sectional area of each individual optical fiber end changes.

38. The panel of claim 34 wherein the shape of the cross-sectional area of each individual optical fiber end is in the shape of a polygon.

39. The panel of claim 34 wherein said buffer material is made of Teflon.

40. The panel assembly of claim 31 wherein said buffer means comprises ferrule means surrounding the remote end of said light cable for packing the optical fiber ends of said cable substantially solid.

41. The panel assembly of claim 31 wherein said remote end of said light cable is polished to a desired finish.

42. The panel assembly of claim 41 further comprising coating means applied to the polished end of said light cable for reflecting certain wavelengths of light.

43. The panel assembly of claim 41 further comprising filter means affixed to the polished end of said light cable for filtering out certain wavelengths of light.

44. The panel assembly of claim 41 further comprising a window adhesively bonded to the polished end of said light cable.

45. The panel assembly of claim 29 for use in radiation curing of epoxies.

46. The panel assembly of claim 29 for use in light curing of epoxies.

47. A method of making a light transmitting panel having one side and an other side opposite said one side comprising the steps of forming a plurality of optical fibers into a panel, with bends the fibers at discrete locations along the length of the fibers to allow light to be emitted therefrom, and applying a coating only to selected areas of the outer surfaces of the bends, such coating extending part way around the sides of said bends and having a refractive index that is different from the refractive index of the optical fibers to change the attenuation of light emitted from such selected areas.

48. The method of claim 47 wherein a coating is applied to such selected areas on one side of the panel having a higher refractive index than the optical fibers, and a coating is applied to such selected areas on the other side of the panel having a lower refractive index than the optical fibers.

49. The method of claim 47 wherein the panel includes a plurality of layers of such optical fibers, and a coating is also applied to selected areas of the outer surfaces of the bends between adjacent layers.

50. The method of claim 47 wherein carrier means are used to apply such coating to such selected areas.

51. The method of claim 50 wherein such carrier means become part of the panel.

52. The method of claim 50 wherein the carrier means is a resin or epoxy-coated film that is heat or radiation cured upon assembly to act as a support to hold the weave spacing and pattern of the woven optical fibers in position and provide protection for the panel from hazardous environments.

53. The method of claim 50 wherein the carrier means includes a prismatic or lenticular film to redirect exit light ray angles of the light being emitted from the panel.

54. The method of claim 50 wherein the carrier means includes a diffuser or transreflector which diffuses light emitted from the panel and reflects ambient light.

55. The method of claim 50 wherein the panel includes a back reflector made of metal which is bendable to permit the panel to be bent into a desired shape.

56. The method of claim 50 wherein metal inserts are provided in the panel to permit the panel to be formed into a desired shape.

57. The method of claim 50 wherein press rolls are used to press the carrier means against the panel to apply the coating to such selected areas.

58. The method of claim 57 wherein the amount of pressure that is applied to the carrier means by the press rolls is variable to vary the amount of surface area of the optical fiber bends that is covered by the coating.

59. The method of claim 47 wherein the amount of surface area of the bends that is covered by the coating is gradually increased or decreased from one end of the panel to the other to adjust the uniformity of light output from the panel.

60. The method of claim 47 wherein rollers are used to apply the coating to such selected areas.

61. The method of claim 60 wherein roller pressure and roller surface type are controlled to control size, shape and location of the coated areas of such selected areas.

62. A light emitting panel having one side and an other side opposite said one side comprising a plurality of woven optical fibers having disruptions or bends at discrete locations along the length of said fibers to allow light to be emitted therefrom, and coating means applied only to selected areas of said disruptions or bends on both sides of said panel, said coating means having a refractive index that changes the attenuation of the light emitted from said selected areas, said coating means on one side of said panel having a higher index of refraction than said optical fibers, and said coating means on the other side of said panel having a lower index of refraction than said optical fibers.

* * * * *